US010610469B2

(12) United States Patent
Bell

(10) Patent No.: US 10,610,469 B2
(45) Date of Patent: Apr. 7, 2020

(54) THERAPEUTIC CALCIUM PHOSPHATE PARTICLES IN USE FOR AESTHETIC OR COSMETIC MEDICINE, AND METHODS OF MANUFACTURE AND USE

(71) Applicant: Leonard B. Miller, Brookline, MA (US)

(72) Inventor: Stephen J. D. Bell, Smyrna, GA (US)

(73) Assignee: Dr. Leonard B. Miller, Brookline, MA (US)

( * ) Notice: Subject to any disclaimer, the term of this patent is extended or adjusted under 35 U.S.C. 154(b) by 0 days.

(21) Appl. No.: 15/229,116

(22) Filed: Aug. 5, 2016

(65) Prior Publication Data

US 2016/0338918 A1 Nov. 24, 2016

Related U.S. Application Data

(63) Continuation of application No. 13/452,715, filed on Apr. 20, 2012, now abandoned, which is a continuation of application No. 11/666,543, filed as application No. PCT/US2005/039496 on Nov. 1, 2005, now abandoned.

(60) Provisional application No. 60/623,958, filed on Nov. 1, 2004.

(51) Int. Cl.
| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 8/24* | (2006.01) |
| *A61Q 19/00* | (2006.01) |
| *A61Q 19/08* | (2006.01) |
| *A61K 8/02* | (2006.01) |
| *A61K 8/36* | (2006.01) |
| *A61K 8/66* | (2006.01) |
| *A61K 8/67* | (2006.01) |
| *A61K 8/73* | (2006.01) |
| *A61K 8/85* | (2006.01) |
| *A61K 8/98* | (2006.01) |

(52) U.S. Cl.
CPC ............. *A61K 8/24* (2013.01); *A61K 8/0245* (2013.01); *A61K 8/36* (2013.01); *A61K 8/66* (2013.01); *A61K 8/671* (2013.01); *A61K 8/676* (2013.01); *A61K 8/678* (2013.01); *A61K 8/73* (2013.01); *A61K 8/85* (2013.01); *A61K 8/981* (2013.01); *A61Q 19/00* (2013.01); *A61Q 19/08* (2013.01); *A61K 2800/10* (2013.01); *A61K 2800/651* (2013.01)

(58) Field of Classification Search
None
See application file for complete search history.

(56) References Cited

U.S. PATENT DOCUMENTS

| | | | |
|---|---|---|---|
| 3,183,545 A | 5/1965 | Bergstrom | |
| 3,382,150 A | 5/1968 | Grass et al. | |
| 3,925,545 A | 12/1975 | Relyveld | |
| 3,983,229 A | 9/1976 | Relyveld | |
| 4,016,252 A * | 4/1977 | Relyveld | 424/212.1 |
| 4,070,454 A | 1/1978 | Relyveld | |
| 4,075,321 A | 2/1978 | Relyveld | |
| 4,350,686 A | 9/1982 | Relyveld et al. | |
| 4,500,512 A | 2/1985 | Barme | |
| 4,552,756 A | 11/1985 | Relyveld et al. | |
| 4,625,019 A | 11/1986 | Relyveld | |
| 4,929,774 A | 5/1990 | Fukamachi et al. | |
| 4,963,526 A | 10/1990 | Ecanow | |
| 5,110,606 A | 5/1992 | Geyer et al. | |
| 5,178,882 A | 1/1993 | Kossovsky et al. | |
| 5,204,382 A | 4/1993 | Wallace et al. | |
| 5,219,577 A | 6/1993 | Kossovsky et al. | |
| 5,306,508 A | 4/1994 | Kossovsky et al. | |
| 5,318,913 A | 6/1994 | Relyveld | |
| 5,334,394 A | 8/1994 | Kossovsky et al. | |
| 5,364,838 A | 11/1994 | Rubsamen | |
| 5,428,066 A | 6/1995 | Larner et al. | |
| 5,441,739 A | 8/1995 | Kossovsky et al. | |
| 5,460,830 A | 10/1995 | Kossovsky et al. | |
| 5,460,831 A | 10/1995 | Kossovsky et al. | |
| 5,462,750 A | 10/1995 | Kossovsky et al. | |
| 5,462,751 A | 10/1995 | Kossovsky et al. | |
| 5,464,634 A | 11/1995 | Kossovsky et al. | |
| 5,469,599 A | 11/1995 | Wurdack | |

(Continued)

FOREIGN PATENT DOCUMENTS

| | | |
|---|---|---|
| EP | 0 326 026 | 6/1992 |
| EP | 0 715 846 | 6/1996 |

(Continued)

OTHER PUBLICATIONS

Supplementary European Search Report of corresponding EP Application No. 05821255.6, dated Aug. 7, 2008.
Abu-Izza K.A. and Lu D.R., "Effect of gastrointestinal protein adsorption on the in vitro release of AZT from ethylcellulose microspheres," Phar. Dev. Technol., 3(4): 495-501 (1998).
Abstracts of papers presented at the 1992 meeting on Modern Approaches to New Vaccines, Including Prevention of AIDS (Cold Spring Harbor), Vaccine 11:92 (1993).
Academic Press Dictionary of Science and Technology, retrieved from http://www.harcourt.com/dictionary/def/2/2/3/1/2231200.html (Nov. 2000).

(Continued)

*Primary Examiner* — Layla Soroush
(74) *Attorney, Agent, or Firm* — Giaccio LLC; Anthony Giaccio

(57) ABSTRACT

Calcium phosphate ("CAP") particles for use in cosmetic, nutraceutic or aesthetic medicine. The particles may be used as carriers for cosmetic, nutraceutic or a factors, as controlled release matrices for the material, and as fillers in cosmetic treatments. The particles may be applied topically or injected or by any other appropriate delivery method.

8 Claims, No Drawings

(56) References Cited

U.S. PATENT DOCUMENTS

| | | | |
|---|---|---|---|
| 5,506,203 | A | 4/1996 | Bäckström et al. |
| 5,549,973 | A | 8/1996 | Majetich et al. |
| 5,580,859 | A | 12/1996 | Felgner et al. |
| 5,593,875 | A | 1/1997 | Wurm et al. |
| 5,595,762 | A | 1/1997 | Derrieu et al. |
| 5,618,800 | A | 4/1997 | Kabra et al. |
| 5,620,896 | A | 4/1997 | Herrmann et al. |
| 5,629,021 | A | 5/1997 | Wright |
| 5,641,515 | A | 6/1997 | Ramtoola |
| 5,648,097 | A | 7/1997 | Nuwayser |
| 5,650,176 | A | 7/1997 | Lee et al. |
| 5,665,382 | A | 9/1997 | Grinstaff et al. |
| 5,676,976 | A | 10/1997 | Lee et al. |
| 5,695,617 | A | 12/1997 | Graiver et al. |
| 5,747,001 | A | 5/1998 | Wiedmann et al. |
| 5,785,975 | A | 7/1998 | Parikh |
| 5,824,638 | A | 10/1998 | Burnside et al. |
| 5,827,822 | A | 10/1998 | Floc'h et al. |
| 5,843,887 | A | 12/1998 | Petit et al. |
| 5,858,398 | A | 1/1999 | Cho |
| 5,866,553 | A | 2/1999 | Donnelly et al. |
| 5,891,420 | A | 4/1999 | Cutie |
| 5,898,028 | A | 4/1999 | Jensen et al. |
| 5,902,789 | A | 5/1999 | Stoltz |
| 5,922,025 | A | 7/1999 | Hubbard |
| 5,985,312 | A | 11/1999 | Jacob et al. |
| 6,007,791 | A | 12/1999 | Coombes et al. |
| 6,017,545 | A | 1/2000 | Modi |
| 6,024,987 | A | 2/2000 | Jettka et al. |
| 6,156,348 | A | 12/2000 | Santos et al. |
| 6,183,803 | B1 | 2/2001 | Morcol et al. |
| 6,187,335 | B1 | 2/2001 | Brey et al. |
| 6,214,368 | B1 | 4/2001 | Lee et al. |
| 6,355,271 | B1 | 3/2002 | Bell et al. |
| 6,537,574 | B1 | 3/2003 | Hubbard |
| 6,541,037 | B1 | 4/2003 | Lee et al. |
| 6,558,612 | B1 | 5/2003 | Hubbard |
| 6,869,445 | B1 | 3/2005 | Johnson |
| 7,148,194 | B2 | 12/2006 | Malik et al. |
| 2001/0021389 | A1 | 9/2001 | Starling et al. |
| 2001/0048925 | A1 | 12/2001 | Bell et al. |
| 2002/0054914 | A1 | 5/2002 | Morcol et al. |
| 2002/0068090 | A1 | 6/2002 | Bell et al. |
| 2002/0197278 | A1* | 12/2002 | Allison ............. A61K 8/64 424/239.1 |
| 2003/0077235 | A1 | 5/2003 | Mansouri et al. |
| 2003/0082232 | A1 | 5/2003 | Lee et al. |
| 2003/0185892 | A1 | 10/2003 | Bell et al. |
| 2004/0115254 | A1 | 6/2004 | Niedzinski et al. |
| 2004/0258763 | A1 | 12/2004 | Bell |
| 2006/0062855 | A1 | 3/2006 | Bell |
| 2007/0292454 | A1 | 12/2007 | Bell et al. |

FOREIGN PATENT DOCUMENTS

| | | |
|---|---|---|
| EP | 1 120 439 A1 | 8/2001 |
| EP | 1514538 | 3/2005 |
| FR | 2 181 426 | 12/1973 |
| FR | 2 466 991 | 4/1981 |
| GB | 1422973 | 1/1976 |
| JP | 9-208491 | 8/1997 |
| JP | 10-114897 | 5/1998 |
| JP | 2001-302431 | 10/2001 |
| JP | 2004-75662 | 3/2004 |
| WO | WO 90/11092 | 10/1990 |
| WO | WO 93/17706 | 9/1993 |
| WO | WO 93/24640 | 12/1993 |
| WO | WO 96/20698 | 7/1996 |
| WO | WO 97/30126 | 8/1997 |
| WO | WO 98/35562 | 8/1998 |
| WO | WO 98/43558 | 10/1998 |
| WO | WO 99/03451 | 1/1999 |
| WO | WO 00/15194 | 3/2000 |
| WO | WO 00/46147 | 8/2000 |
| WO | WO 02/064112 | 8/2002 |
| WO | WO 03/51394 | 6/2003 |
| WO | WO 04/026453 | 4/2004 |
| WO | WO 04/050065 | 6/2004 |
| WO | WO 05/099668 | 10/2005 |
| WO | WO 06/050368 | 5/2006 |
| WO | WO 06/073503 | 7/2006 |

OTHER PUBLICATIONS

Acsadi, G. et al., "Human dystrophin expression in mdx mice after intramuscular injection of DNA constructs," Nature 352: 815-818 (1991).

Al-Achi, A. & Greenwood, R., "Erythrocytes as Oral Delivery Systems for Human Insulin," Drug Dev. and Ind. Pharm., 24(1): 67-72 (1998).

Aldovini, A. & R.A. Young, "Humoral and cell-mediated immune responses to live recombinant BCG-HIV vaccines," Nature 351: 479-482 (1991).

Alward, W.L.M, "Medical Management of Glaucoma," N. Eng. J. Med., 339(18): 1298-1307 (1998).

Bartus, R.T. et al., "Sustained Delivery of Proteins for Novel Therapeutic Products," Science, 281 (5380):1611-1162 (1998).

Bastin, J. et al., Use of Synthetic Peptides of Influenza Nucleoprotein to Define Epitopes Recognized by Class I-Restricted Cytotoxic T Lymphocytes,: J. Exp. Med., 165(4): 1508-1523 (1987).

Bayomi, M.A. et al., "Preparation of casein-chitosan microspheres containing diltiazem hydrochloride by an aqueous coacervation technique," Pharm. Acta. Helv. 73: 187-192 (1998).

Bennink, J.R. and Yewdell, J.W., "Recombinant Vaccinia Viruses as Vectors for Studuying T Lymphocyte Specificity and Function," Curr. Top. Microbiol. Immunol., 163:153-184 (1990).

Benvenisty, N. and Reshef, L., "Direct introduction of genes into rats and expression of genes," Proc. Natl. Acad. Sci. , vol. 83, 9551-9555 (1986).

Bochot, A. et al., "Intravitreal Delivery of Oligonucleotides by Sterically Stabilized Liposomes," Invest. Opthalmol. Vis. Sci., 43(1): 253-259 (2002).

Bousquet, J. et al., "Allergen immunotherapy: therapeutic vaccines for allergic diseases," Ann Allergy, Athsma, Imm. 81:401-405 (1998).

Bousquet, J., "Allergy diagnosis," Allergy Tests & Therapy, The Buyer's Guide to Respiratory Care Products, pp. 8-10.

Brubaker, R.F., Mechanism of Action of Bimatoprost (Lumigan™) Survey of Opthal. 45(4): S347-S351 (2001).

Brubaker, R.F., "Measurement of Aqueous Flow by Fluorophotometry," The Glaucomas, Chapter 17, 337-344 (1989).

Bulgarelli, E. et al., "Effect of matrix composition and process conditions on casein-gelatin beads floating properties," Int. J. Pharm., 198:157-165 (2000).

Bulgarelli, E. et al., "Casein/gelatin beads: I. Cross-linker solution composition effect on cross-linking degree," Int. J. Pharm, 190(2):175-182 (1999).

Carbone, F.R. and Bevan, M.J. "Induction of Ovalbumin-specific cytotoxic T cells by in vivo peptide immunization," J. Exp. Med., 169(1): 603-612 (1989).

Chen, Y. et al., "Comparison of albumin and casein microspheres as a carrier for doxorubicin," J. Pharm. Pharmacol., 39: 978-985 (1987).

Chu, E. et al., "Mechanisms and Sites of Ocular Action of 7-Hydroxy-2-dipropylaminotetralin: A Dopamine$_3$ Receptor Agonist[1]," J. Pharma. & Exper. Therap., 293(3): 710-716 (2000).

Chu, E. et al., "Potential Sites of Action of TNPA: A Dopamine-2 Receptor Agonist," Exp. Eye Res. 69: 611-616 (1999).

Chu, T.H. et al., "Biodegradable Calcium Phosphate Nanoparticles as a New Vehicle for Delivery of a Potential Ocular Hypotensive Agent," Ocular Pharma. & Thera., 18(6); 507-514 (2002).

Choudhari, K.B. et al., "Liposomes as a carrier for oral administration of insulin: effect of formulation factors," 11(3) Journal of Microencapsulation, 319-325 (1994).

Collins, D.S. et al., "Processing of exogenous liposome-encapsulated antigens in vivo generates class I MCH-restricted T cell responses," J. Immunol., 148(11): 3336-3341 (1992).

(56) References Cited

OTHER PUBLICATIONS

Cooney, E.L. et al., "Safety of and immunological response to a recombinant vaccinia virus vaccine expressing HIV envelope glycoprotein," Lancet, 337:567-572 (1991).
Cox, G.J.M. et al., "Bovine Herpesvirus 1: Immune Responese in Mice and cattle Injected with Plasmid DNA," J. Virol. 67(9): 5664-5667 (1993).
Damge, C. et al., "New Approach for Oral Administration Insulin with Polyalkylcyanoacrylate Nanocapsules as Drug Carrier," Diabetes 37: 246-251(1988).
Damge, C. et al., "Poly(alkyl cyanoacrylate) Nanospheres for Oral Administration of Insulin," J. Pharm. Sci. 86(12):1403-1409 (1997).
De Campos, A. et al., "Chitosan nanoparticles: a new vehicle for the improvement of the delivery of drugs to the ocular surface. Application to cyclosporin A," Int. J. Pharm. 224:159-168 (2001).
Deres, K. et al., "In vivo priming of virus-specific cytoxic T lymphocytes with synthetic lipoprotein vaccine," Nature, 342:561-564 (1989).
Donnelly, J.J. et al., "DNA Vaccines," Annu. Rev. Immunol., 15: 617-648 (1997).
Edgington, S.M., "Turning on Tumor-Fightig T-Cells," Biotechnology, 11:1117-1119 (1993).
Edwards, D.A. et al., "Large Porous Particles for Pulmonary Drug Delivery," Science, 276:1868 (1997).
Feng, Zhen-qing, et al., "Nanoparticles as a vaccine adjuvant of anti-idiotypic antibody against schistosomiasis", Chinese Medicine Journal, 2004, vol. 117, No. 1, pp. 83-87.
Friedman, T., "Progress Toward Human Gene Therapy," Science, 244, 1275-1281 (1989).
Furth, P.A. et al., "Gene Transfer into Somatic Tissues by Jet Injection," Analytical Biochemistry, 205(2): 365-368 (1992).
Gardner, I. et al., "Cell-mediated cytotoxicity against ectromelia virus-infected target cells," Eur. J. Immunol., 4:68-72 (1974).
Goto, N. et al., "Local tissue irritating effects and adjuvant activities of calcium phosphate and aluminum hydroxide with different physical properties," Vaccine, 15(1213): 1364-1371 (1997).
Goto, N. et al., "Studies on the toxicities of aluminum hydroxide and calcium phosphate as immunological adjuvants for vaccines," Vaccine, 11(9): 914-918 (1993).
Goto, N., "Toxicity of Aluminum Compounds as an Adjuvant for Vaccines," Aluminum Toxicity in Infants' Health and Disease, Aluminum Toxicity in Infants' Health and Disease, Chapter 15, pp. 208-224 (1997).
Gupta, R. K. et al., "Adjuvant Properties of Aluminum and Calcium Compounds," *Vaccine Design: The Subunit and Adjuvant Approach*, Chapter 8, 229-248 (1995).
Hahn, C.S. et al., "Infectious Sindbis virus transient expression vectors for studying antigen processing and presentation," Proc. Natl. Acad. Sci. (USA) 89: 2679-2683 (1992).
Hansen, E. et al. "Strong expression of foreign genes following direct injection into fish muscle," FEBS Lett. 290, Nos. 1,2, pp. 73-76 (1991).
He, Q. et al. "Calcium Phosphate Nanoparticles Induce Mucosal Immunity and Protection against Herpes Simplex Virus Type-2," Clin & Diag. Lab., 9(5): 1021-1024 (Sep. 2002).
He, Q. et al., "Calcium Phosphate Nanoparticle Adjuvant," Clin. & Diag. Lab. Immuno. 7(6): 899-903 (2000).
Heelan, B.A. et al., "In vitro analy sis of the release of incorporated agents from sodium caseinate microspheres," J. Microencapsul., 14(1): 63-78 (1997).
Hosny, E.A. et al., "Promotion of oral insulin adsorption in diabetic rabbits using pH-dependent coated capsules containing sodium cholate," Pharm. Acta. Helv., 72: 203-207 (1997).
Hosny, E. A. et al., "Hypoglycemic Effect of Oral Insulin in Diabetic Rabbits Using pH-Dependent Coated Capsules Containing Sodium Salicylate Without and With Sodium Cholate," 24(3), Drug Development and Industrial Pharmacy, 24(3):307-311 (1998).
Hoyng, P.F.J and Van Beek, L.M., "Pharmacological Therapy for Glaucoma," Drugs 59(3) : 431-434 (2000).

Ickovic, M.R. et al., "Calcium-Phosphate-Adjuvanted Allergens: Total and Specific IgE Levels Before and After Immunotherapy with House Dust and Dermatophagoides Pteronyssinus Extracts," Ann. Immunolo. (Inst. Pasteur) 134 D: 385-398 (1983).
Jiao, S. et al., "Direct Gene Transfer into Nonhuman Primate Myofibers In Vivo," Hum. Gene Therapy 3:21-33 (1992).
Kato, et al., "Relationship between Hemolytic Activity and Absorption Capacity of Aluminum Hydroxide and Calcium Phosphate as Immunological Adjuvants for Biologicals," Microbiol. Immunol., 38(7): 543-548 (1994).
Kimura,T. et al. "Oral administration of insulin as poly(vinyl alcohol)-gel spheres in diabetic rats," Biol. Pharm. Bulletin 19(6): 897-900 (1996).
Kitsis, R.N. et al., "Hormonal modulation of a gene injected into rat heart in vivo," Proc. Natl. Acad. Sci. (USA) 88: 4138-4142 (1991).
Knepp, W.A. "Synthesis, properties, and intratumoral evaluation of mitoxantrone-loaded casein microspheres in Lewis lung carcinoma," J. Pharm. Pharmacol., 45: 887-891 (1993).
Lamprecht, A. et al., "Biodegradable Nanoparticles for Targeted Drug Delivery in Treatment of Inflammatory Bowel Disease," J. Pharm. Exp. Thera., 299(2): 775-781 (2001).
Latha, M.S. et al., "Progesterone release from glutaraldehyde cross-linked casein microspheres: in vitro studies and in vivo response in rabbits," Contraception, 61: 329-334 (2000).
Latha, "Glutaraldehyde cross-linked bovine casein microspheres as a matrix for the controlled release of theophylline: in vitro studies," J. Pharma. Pharmacol., 46: 8-13 (1994).
Latha, M.S. and Jayakrishnan A., "A new method for the synthesis of smooth, round, hydrophilic protein microspheres using low concentrations of polymeric dispersing agents," J. Microencapsul., 12(1):7-12 (1995).
Latha, M.S. et al., "Casein as a Carrier Matrix for 5-Fluorouracil: Drug Release from Microspheres, Drug protein Conjugates and In-vivo Degradation of Microspheres in Rat Muscle," J. Pharm. Pharmacol., vol. 46, pp. 858-862 (1994).
Lecadet, A. et al., "Specific desensitization with the help of allergens adsorbed on calcium phosphates (Institut Pasteur) Clinical and biological study of 107 cases," Allergie et Immunologie, 20(4): 153-158 (1988).
Lelong, M. & Miersman, R., "Long-term tolerance of specific hyposensitization with calcium phosphate adjuvenated mite allergens," Allergy and Immunology, 18(9): 15-18 (1986).
Lery, L., "Haemolytic activity of calcium phosphate adjuvant," Vaccine 12(5): 475 (1994).
Li, V.H.K., et al., "Ocular drug delivery of progesterone using nanoparticles," J. Microencaps. 3(3): 213-218 (1986).
Lin, H. et al., "Expression of Recombinant Genes in Myocardium In Vivo after Direct Injection of DNA," Circulation 82(6): 2217-2221 (1990).
Lin, Y. & Askonas, B.A. "Biological Properties of an Influenza A Virus-Specific Killer T Cell Clone," J. Exp. Med. 154(1): 225-234 (1981).
Lowman, A.M. et al. "Oral Delivery of Insulin Using pH-Responsive Complexation Gels," 88(9) J. Pharm. Sci., 88(9) pp. 933-937 (1999).
Maniatis et al., *Molecular Cloning, A Laboratory Manual*, Cold Spring Harbor Laboratory Press, $2^{nd}$ ed., New York 1.0-19.0 (1989). (Table of Contents only).
Mascola, L. et al., "Surveillance of Listeriosis in Los Angeles County, 1985-1986," Arch. Intern. Med., 149(7): 1569-1572 (1989).
McMichael, A.J. et al., "Cytoxic T-Cell Immunity to Influenza," New Engl. J. Med., 309(1): 13-17 (1983).
McMichael, A.J. et al., "Recognition of Influenza A Virus Nucleoprotein by Human Cytotoxic T Lymphocytes," J. Gen. Virol., 67: 719-726 (1986).
Michel, C. et al, "The Effect of Site of Administration in the Gastrointestinal Tract on the Absorption of Insulin from Nanocapsules in Diabetic Rats," J. Pharm. Pharmacol., 43:1-5 (1991).
Miller, A.D. "Reiroviral Vectors," Curr. Top. Microbiol. Immunol., 158, 3-24 (1992).
Montgomery, D.L. et al. "Heterologous and Homologous Protection Against Influenza A by DNA Vaccination: Optimization of DNA Vectors," DNA and Cell Biol. 12(9): 777-783 (1993).

(56) References Cited

OTHER PUBLICATIONS

Musabayane, C.T. et al., "Orally administered, insulin-loaded amidated pectin hydogel beads sustain plasma concentrations of insulin in streptozotocin-diabetic rats," J. Endocronology, 164(1): 1-6 (2000).
Naylor, L.J. et al., "Comparison of the mechanism of dissolution of hydrocortisone in simple and mixed micelle systems," Pharm. Res. 10(6): 865-870 (1993).
Neefjes, J.J. & Momburg, F., "Cell biology of antigen presentation," Curr. Opin. Immuno. 5(1): 27-34 (1993).
Newman, M.J. et al., "Saponin Adjuvant Induction of Ovalbumin-Specific CD8+Cytotoxic T Lymphocyte Responses," The J. of Immunology (1992) vol. 148 (8), pp. 2357-2362.
Ogidigben, M.J. et al., "Comparative Effects of Alpha-2 and DA-2 Agonists on Intraocular Pressure in Pigmented and Nonpigmented Rabbits," J. Ocular Pharma. 9(3): 187-199 (1993).
Ogidigben, M. et al., "Ocular Hypotensive Action of a Dopaminergic $(DA_2)$ Agonist, 2, 10, 11-trilaydroxy-N-n-propylnoraporphine[1]," J. Pharmaco. Exp. Therap. 267:2, 822-827 (1993).
O'Hehir, R.E., "Immunology and allergy," Med. J. of Aus. 176(1): 22 (2002). Retrieved: www.mja.com.au.
Olivares, E. et al., "Effects of a Protective Hydrolized Casein Diet Upon the Metabolic and Secretory Responses of Pancreatic Islets to IL-1β, Cytokine Production by Mesenteric Lymph Node Cells, Mitogenic and Biosynthetic Activities and Peyers' Patch Cells, and Mitogenic Activity and Pancreatic Lymph Node Cells from Control and Diabetes-Prone BB Rats," Molecular Genetics and Metabolism, 68(3): 379-390 (1999).
Potter, D.E., "Do Dopamine and Dopamine Receptors have Roles in Modulating Function in the Anterior Segment?: The Evidence," Progress in Retinal & Eye Res., 15(1): 103-111 (1995).
Redfield et al., "Disseminated Vaccinia in a Military Recruit with Human Immunodeficiency Virus (HIV) Disease," New Engl. J. Med., 316(11): 673-676 (1987).
Relyveld, E.H., et al. "Récents progrès en immunothérapie spécifique à l'aide d'allergènes adsorbès sur phosphate de calcium," Allergie et Immunologie 16(1): 60-71 (1984). (English-language abstract provided herewith).
Relyveld, E.H. et al., "Calcium Phosphate Adjuvanted Allergens," Annals of Allergy 54(6): 521-528 (1985).
Relyveld, E.H., "Preparation and Use of Calcium Phosphate Adsorbed Vaccines," Dev. Bio. Standards 65: 131-136 (1986).
Robinson, H.L. et al., "Protection against a lethal influenza virus challenge by immunization with a haegmagglutinin-expressing palsmid DAN," Vaccine 11(9): 957-960 (1993).
Rolland, J., "New Vaccines for Allergic Rhinitis," Dept. Patho. Immunol., Monash University Medical School, Alfred Hospital, Melbourne.
Rowland, R.N. et al., "The stability of liposome's in vitro to pH, bile salts and pancreatic lipase," Biochem. Biophsy. Acta., 620(3):400-409 (1980).
Sato, Y et al., "Immunostimulatory DNA Sequences Necessary for Effetive Intradermal Gene Immunization," Science 273: 352-354 (1996).
Santinho, A. et al., "Influence of formulation on the physiochemical properties of casein microparticles," Intl. J. Pharm. 186(2): 191-198 (1999).
Schafer, R. et al., "Induction of a cellular immune response to a foreign antigen by a recombinant *Listeria monocytogenes* Vaccine," J. Immunol., 149(1):53-59 (1992).
Service, R.E., "Drug Delivery Takes a Deep Breath," Science, 277:1199-1200 (1997).
Stover, C.K. et al., "New Use of BCG for Recombinant Vaccines," Nature 351: 456-460 (1991).
Takahashi, H. et al., "Induction of CD8 cytotoxic T cells by immunization with purified HIV-1 envelope protein in ISCOMs," Nature, 344: 152-154 (1990).
Tang, D. et al., "Genetic immunization with purified HIV-1 envelope protein in ISCOMs," Nature, 356: 873-875 (1992).
Taylor, P.M. and Askonas, B.A. "Influenza nucleoprotein-specific cytotoxic T-cell clones are protective in vivo," Immunol., 58(1) : 417-420 (1986).
Tragl, et al., "Oral administration of insulin by means of liposome's in animal experiments," (author's trans.), Wien Klin Wochenschr, 91(13): 448-451 (1979). (English-language abstract).
Townsend, A. et al. "Antigen Recognition by Class I-Restricted T Lymphocyes," Annu. Rev. Immunol., 7: 601-624 (1989).
Townsend, A. et al., "The Epitodes of Influenza Nucleoprotein Recognized by Cytotoxic T Lymphocytes Can be defined with Short Synthetic Peptides," Cell 44: 959-968 (1986).
Tozaki, H. et al., "Chitosan Capsules for Colon-Specific Drug Delivery: Improvement of Insulin Absorption from the Rat Colon," J. Pharm., Sci., 86(9): 1016-1021 (1997).
Ulmer, J.B. et al., "Heterologous Protection Against Influenza by Injection of DNA Encoding a Viral Protein," Science, 259: 1745-1749 (1993).
Wang, B. et al., "Gene inoculation generates immune responses against human immunodeficiency virus type I," Proc. Natl. Acad. Sci. 90: 4156-4160 (May 1993).
Wang, S. et al., "Enhanced type I immune response to a hepatitis B DNA vaccine by formulation with calcium- or aluminum phosphate," Vaccine, 18: 1227-1235 (2000).
Weiner, G.J. et al., "Immunostimulatory oligodeoxynucleotides containing the CpG motif are effective as immune adjuvants in tumor antigen immunization," Proc. Natl. Acad. Sci. (USA) 94(19): 10833-10837 (1997).
Wilmott, N. et al., "Biodegradation rate of embolized protein microspheres in lung, liver and kidney of rats," J. Pharm. Pharmacol., 41: 433-438 (1989).
Wilmott, N. et al., "Doxorubicin-loaded casein microspheres: protein nature of drug incorporation," J. Pharm. Pharacol, 44: 472-475 (1992).
Wolff, J.A. et al., "Long-term persistence of plasmid DNA and foreign gene expression in mouse muscle," Human Mol. Genet. 1(6) : 363-369 (1992).
Wolff, J.A. et al., "Direct Gene Transfer into Mouse Muscle in Vivo," Science 247: 1465-1468 (1990).
Yablonski, M.E. et al., "A Fluorophotometric Study of the Effect of Topical Timolol on Aqueous Humor Dynamics," Exp. Eye Res. 27: 135-142 (1978).
Yap, K.L. and Ada, G.L., "Transfer of specific cytoxic T lymphocytes protects mice inoculated with influenza virus," Nature, 273: 238-239 (1978).
Yewdell, J.W. et al., "Influenza A virus nucleoprotein is a major target antigen for cross-reactive anti-influenza A virus cytotoxic T lymphocytes," Proc. Natl. Acad. Sci. (USA) 82:1785-1789 (1985).
Zhu, N. et al., "Systematic Gene Expression After Intravenous DNA Delivery into Adult Mice," Science 261: 209-211 (1993).
FDA-CDER, Summer Minutes, Allergenic Products Advisory Committee, Meeting 5, Jun. 25-26, 1987.
"The Sugar Blues?" Retrieved from http://vaxa.com/html/669.cfm on Sep. 10, 2000.
International Search Report and Written Opinion, PCT/US2005/039496 dated Jul. 20, 2006.

* cited by examiner

THERAPEUTIC CALCIUM PHOSPHATE PARTICLES IN USE FOR AESTHETIC OR COSMETIC MEDICINE, AND METHODS OF MANUFACTURE AND USE

This application is a continuation of U.S. application Ser. No. 13/452,715, filed Apr. 20, 2012, which is a continuation of U.S. application Ser. No. 11/666,543, filed May 8, 2008, now abandoned, which is a National Phase Application of International PCT Application Serial No. PCT/US2005/039496, filed Nov. 1, 2005, which claims the benefit of U.S. Provisional Patent Application Ser. No. 60/623,958, filed Nov. 1, 2004, the entire contents of each of which are hereby incorporated by reference.

BACKGROUND OF INVENTION

Field of the Invention

The present invention relates to novel calcium phosphate core particles for use in aesthetic medicine, to methods of making them, and to methods of using them in corrective or cosmetic surgery, as filler, for the sustained release of cosmetic medicines, and as a delivery vehicle for pharmaceutical agents, nutraceuticals, growth factors, and/or tissue repair chemicals and biochemicals.

Description of Related Art

Nanometer scale particles have been proposed for use as carrier particles, as supports for biologically active molecules, such as proteins, and as decoy viruses. See U.S. Pat. Nos. 5,178,882; 5,219,577; 5,306,508; 5,334,394; 5,460,830; 5,460,831; 5,462,750; and 5,464,634, the entire contents of each of which are hereby incorporated by reference. The particles disclosed in the above-referenced patents, however, are generally extremely small, in the 10-200 nm size range. Particles of this size are difficult to make with any, degree of consistency, and their morphology is not described in any detail. None of these patents disclose the use of nanoparticles as sustained release matrices. Furthermore, these patents do not disclose the use of calcium phosphate particles as either adjuvants or delivery vehicles for aesthetic medicine or treatments.

There has been a suggestion in the literature to use calcium phosphate particles as vaccine adjuvants, but calcium phosphate particles have generally been considered an unsuitable alternative to other adjuvants due to inferior adjuvanting activity. See, e.g., Goto et al., Vaccine, vol. 15, no. 12/13 (1997). Moreover, the calcium phosphate evaluated was typically microparticulate (>1000 nm diameter) and possessed a rough and oblong morphology, in contrast to the core particles of the present invention.

Therefore, an important need remains for calcium phosphate core particles useful as core materials or carriers for biologically active moieties that can be produced simply and consistently. A further need remains for calcium phosphate core particles that can be effectively used as adjuvants and delivery vehicles for aesthetic medicines and treatments, and as controlled release matrices for use in cosmetic, nutraceutic, or aesthetic applications.

The inventor's issued patent and pending patent application disclose many varieties of CAP particles and their methods of use. U.S. Pat. No. 6,355,271, which is hereby incorporated by reference, discloses the inventor's novel therapeutic calcium phosphate particles and methods of their manufacture and use. Further, pending U.S. patent application Ser. Nos. 09/794,576, 09/932,538, 09/932,503, 10/306,062, and 10/824,097 disclose other compositions and uses of the inventor's calcium phosphate particles. Each of these applications is hereby incorporated by reference.

SUMMARY

The present invention relates to novel calcium phosphate ("CAP") core particles, to methods of making them, to methods of using them in cosmetic, nutraceutic, or aesthetic medicine, as cores or carriers for biologically active material, as controlled release matrices for biologically active material, and as fillers for aesthetic treatments. The core particles preferably have a diameter between about 200 nm and about 4000 nm, more particularly between about 300 nm and about 1000 nm, and they have a substantially spherical shape and a substantially smooth surface.

The present invention also relates to the novel calcium phosphate core particles having a material coated on the surface of the core particles, and/or dispersed or impregnated within the core particles, to methods of making them, and to methods of using them.

The present invention also relates to combinations of this novel core particle having at least a partial coating of a surface modifying agent or a surface modifying agent impregnated therein or both. If a cosmetic, nutraceutic, or aesthetic material is at least partially coated on the particle, the material may be optionally attached to the particle by the surface modifying agent, which acts as a biological "glue," such as cellobiose or polyethylene glycol (PEG), although other biological glues are usable with the present invention.

The invention also relates to combinations of this novel core particle with cosmetic, nutraceutic, or aesthetic agents integrated into the core particle, forming a controlled release matrix that releases the material into a patient over time.

A further embodiment relates the use of the novel calcium phosphate particles as a stand-alone filler in cosmetic, nutraceutic, or reconstructive surgery. The calcium phosphate particles may be injected intramuscularly or intratissue and may be used as a solid or semi-solid base, or as a support foundation. Various uses for the injection of calcium phosphate particles include use as a filler in an effort to smooth skin and reduce wrinkles or other unwanted skin irregularities. Other embodiments of the invention relate to a combination of the particles and a microdermabrasion component for use in treating the surface of a patient's skin. Further embodiments relate to the use of a combination of the particles and another skin treatment agent that can be applied topically, applied to mucosal surfaces of the body, or injected.

In a specific embodiment, the invention relates to methods of providing cosmetic, nutraceutic, or aesthetic agents or medicines (which are described in more detail below and will be referred to collectively as "aesthetic factors") to patients in need thereof by administration of the novel core particles in combination or in conjunction with agent useful in cosmetic, nutraceutic, or aesthetic applications, wherein the agent is at least partially coated on the core particle and/or integrated therein. It is thought that the calcium phosphate core particles of this embodiment may significantly increase the efficacy of the agents with which they are administered, by enhancing the magnitudes, qualities, and/or durations of the patient's responses. This extended bioavailability may reduce the amount of agent needed to attain the desired effect, thus resulting in a decrease in both cost and safety concerns. The calcium phosphate particles may also improve the "half life" or stability of the "active" or aesthetic factor that is co-administered. The calcium phosphate particles of this embodiment may be provided to the patient by any method previously described in the inventor's patent applications, including topical application, to mucosal surfaces of the body, and delivery through injection.

In another embodiment, the invention also relates to the use of the inventor's novel calcium phosphate particles as a delivery vehicle in cosmetic, nutraceutic, or aesthetic procedures. The calcium phosphate particles of the present invention may be delivered topically, transdermally, intradermally, subdermally, subcutaneously, transmucosally, or through intramuscular or intratissue injection. Examples of agents which may be delivered through the invention's novel calcium phosphate particles include vaccines, anti-pain medications, anti-inflammatory medications, anti-cancer medications and antibiotics, anti-acne treatments, pore reducing treatments, sun-damage treatments, eczema or other skin condition treatments, broken capillary treatments, vitamins, minerals, herbs, muscle relaxants, growth factors, tissue repair chemicals, blockers of muscle contraction, in combination with other known fillers, and/or biochemicals. Examples of such agents include, but are not limited to, vitamins, minerals, nutrients, epidermal growth factors, fibroblast growth factor, collagen, Interleukin-1, and tumor necrosis factor. Alternatively, if preferred, agents such as anti-epidermal growth factor, anti-fibroblast growth factor, anti-IL-1, and anti-tumor necrosis factor may be delivered.

The present invention also relates to methods of treating physiologic, metabolic, cosmetic and aesthetic medical conditions by administering effective amounts of the calcium phosphate particles either as "stand alone" entities, or, in combination with cosmetic medicines to a patient in need thereof. The therapeutic compositions of the present invention are highly stable and may exhibit enhanced bioavailability, improved stability, efficacy, or increased "half life" after in vivo administration. These therapeutic compositions also exhibit preferable biodynamics including controlled release of cosmetic, nutraceutic, and aesthetic agents . . . . The present invention also relates to methods of preparing the novel calcium phosphate core particles described above, such as the core particles for use individually, the core particles having material at least partially coated on the surface, and the core particles having material impregnated therein.

DETAILED DESCRIPTION OF SPECIFIC EMBODIMENTS

The present invention relates generally to novel calcium phosphate core particles, to methods of making them, and to methods of using the core particles as adjuvants, for functional enhancement of drugs and therapeutic factors, or as delivery vehicles for nutraceutic and aesthetic treatments, as controlled release matrices for aesthetic treatments, and as "stand-alone" fillers for use in cosmetic treatments. The present invention also relates to the novel calcium phosphate core particles having a desired material at least partially coated on the surface of the core particles, or dispersed or impregnated within the core particles, to methods of making them, and to methods of using them. Non-limiting examples of a suitable material to be at least partially coated on the surface of the core particle or impregnated therein include aesthetic factors that are intended to treat wrinkles and/or skin imperfections, to enhance skin elasticity, moisture, and/or appearance; to deliver skin-enhancing minerals and vitamins; to act as a filler; to abrade the surface of the skin such as dermabrasion or exfoliation; to provide nourishment (for example, in the form of nutrients or vitamins, minerals or growth factors, all collectively referred to as "nutraceuticals") to underling skin cells; to treat other skin conditions such as eczema, acne, rosacea, moles, wrinkles, and so forth.

The core particles of the present invention may optionally have at least a partial coating of a surface modifying agent, which may help adhere the above-mentioned material to the core particle, or may have a surface modifying agent impregnating the particle, or both. A preferred form of such an agent is polyethylene glycol or other mono- or disaccharides.

One embodiment of the present invention relates to calcium phosphate core particles suitable for delivering, adjuvanting or enhancing the respective chemical and/or biological functions of various nutraceuticals, and cosmetic or aesthetic factors, the particles being administrable in their uncoated state. The core particles are also suitable for use as supports for cosmetic, nutraceutic, or aesthetic agents and for providing a controlled or sustained release matrix for such products and medicines. Another embodiment of the present invention relates to the use of the calcium phosphate particles as a filler, in other words, the particles may be delivered as "stand-alone" particles.

The calcium phosphate core particles of the present invention have an average particle size between about 200 nm and about 4000 nm, more particularly, between about 200 nm and about 2000 nm. For the applications described herein, an average particle size of between about 200 nm and 1000 nm is sufficient and desirable. The core particles of the present invention have a morphology that is generally and substantially spherical in shape and a surface that is substantially smooth.

The term "substantially smooth" is used herein to mean essentially no surface features or irregularities having a size of 100 nm or larger. The core particles may be faceted or angular and still fall within this definition, as long as the facets do not contain many surface irregularities of the type described above. The term "substantially spherical" is used herein to refer to particles that are substantially round or oval in shape, and includes particles that are unfaceted and smooth, or that have very few facets, as well as particles that are polyhedral having several or numerous facets.

In another embodiment, the core particles of the present invention can also be at least partially coated with material, wherein the material is disposed on the surface of the core particle and optionally held in place by a surface modifying agent sufficient to bind the material to the core particle without denaturing the material.

Surface modifying agents suitable for use in the present invention include substances that provide a threshold surface energy to the core particle sufficient to bind material to the surface of the core particle, without denaturing the material. Example of suitable surface modifying agents include those described in U.S. Pat. Nos. 5,460,830, 5,462,751, 5,460,831, and 5,219,577, the entire contents of each of which are incorporated herein by reference. Non-limiting examples of suitable surface modifying agents may include basic or modified sugars, such as cellobiose, or oligonucleotides, which are all described in U.S. Pat. No. 5,219,577. Suitable surface modifying agents also include carbohydrates, carbohydrate derivatives, and other macromolecules with carbohydrate-like components characterized by the abundance of —OH side groups, as described, for example, in U.S. Pat. No. 5,460,830. Polyethylene glycol (PEG) is a particularly suitable surface modifying agent.

The particles of this invention may be combined with any of the wrinkle treatments, skin fillers, dermal stimulators, topical treatments, vitamins and minerals, and/or vein therapy treatments described below, or any similar agents.

(The examples provided in this application are intended to be non-limiting.) The particles may additionally or alternatively be delivered alone to act as a skin filler.

In a specific embodiment, the particles may be formed as described in Example 1, and if they are intended to be used as a carrier of an aesthetic factor, the composition (referred to in the Example and in the below descriptions as "an aesthetic factor") may either be added to the formulation during particle formation so that it is at least partially impregnated into the particles or it may be coated onto the particles, or a combination of both.

The below example provides only one way that can be used to make the core particles of the present invention, and it should be understood that other methods can be provided and are considered within the scope of this invention. Moreover, as previously stated, the examples of materials that may form an aesthetic factor or that may be delivered using the particles of the present invention are provided merely as examples, and it is intended that any other aesthetic treatments or medicines may be delivered or adjuvanted using the described particles.

Example

A 12.5 mM solution of $CaCl_2$ is prepared (for example, by mixing 1 to 2 g of $CaCl_2$ into 800 mL of sterile GDP water under aseptic conditions until completely dissolved, and diluting it to 1 L, and then filtering). A 15.625 mM solution of sodium citrate is then prepared (for example, by dissolving 0.919 g of sodium citrate into 200 mL of sterile GDP water with mixing using aseptic techniques and filtered). Then, a 12.5 mM solution of dibasic sodium phosphate is prepared (for example, by dissolving 1.775 g sodium phosphate into 1 L of sterile GDP water with mixing using aseptic techniques and filtered). All solutions were stored at room temperature.

The calcium chloride solution is combined with the sodium citrate solution and thoroughly mixed. The sodium phosphate solution is then added with mixing. Turbidity appears as particles began to form. In certain embodiments, the particles may be used by themselves (as fillers), which will be described in more detail below. In other embodiments, an aesthetic factor (which is intended to be any aesthetic factor described in this application, as well any other aesthetic factors or components that may be used to treat skin or otherwise enhance the skin's appearance) may be added during the formation of these particles. This is intended to form particles that have an aesthetic factor at least partially embedded therein.

In a further embodiment, an aesthetic factor is added to a solution of particles that have already been formed. In this instance, the above suspension is allowed to mix for several minutes and mixing may be continued for about 48 hours under a laminar flow hood. Following mixing, the particles may be sonicated on a high power setting for about 30 minutes at room temperature. Following preparation, the particles may also be allowed to equilibrate for approximately seven days before use.

Cellobiose (or polyethylene glycol or any another biological "glue") may then be applied to the particles by suspending them in a solution of the glue added to the suspension of calcium phosphate particles, typically at a ratio of 1 mL of "glue" to 20 mL of particle suspension. The mixture is gently mixed and allowed to stand overnight. The at least partially coated particles are then contacted with a solution of an aesthetic factor.

I. Wrinkle Treatments

A first embodiment of the invention relates to calcium phosphate particles as core carriers or adjuvants and delivered in combination with a wrinkle treatment, such as a muscle relaxant or a skin filler, which may be the aesthetic factor in the above example. Another embodiment relates to the particles delivered alone for use as a skin filler. Facial lines and wrinkles are caused by the destruction of the support layer within the skin. Injectable treatments, such as Botox, can relax underlying muscles and allow the skin to relax. Injectable implants such as collagen and restylane replenish the skin's natural support layer, smoothing facial lines and many types of scars. Such treatments are typically injected, although it is foreseeable that such treatments may also be delivered topically or otherwise at some point in the future.

There are two different kinds of facial wrinkles—static and dynamic. Static wrinkles are the lines and folds that are on the face all the time. Dynamic wrinkles are the lines that appear when there is muscle movement resulting in facial expressions (crow's feet, frown or forehead lines). Botox® is designed to stop dynamic wrinkles. It prevents the nerves ending from communicating to the muscle to contract. Botox®, or Botulinum Toxin type A, is an FDA approved treatment that is injected into the muscles that cause lines and wrinkles. Commonly treated areas include frown lines between the eyebrows, wrinkles around the eyes, and horizontal lines on the forehead. As the treated muscle weakens, the skin overlying the muscle also relaxes and wrinkles begin to soften. Botox (or any other muscle weakening component or composition) may be used as an aesthetic factor in the above example. Those of ordinary skill in the art would be able to determine appropriate concentration and dosage amounts.

Another type of wrinkle treatment is a skin filler. Botox® is not a filler. It will not fill or plump up lines or depressions in the skin that are present the face is at rest. In order to improve deep set static lines, there are treatments, called "skin fillers," that plump up the lines. The delivery of the calcium phosphate particles described herein can be used as a skin filler. They may be delivered alone, in combination with a pharmaceutically acceptable excipient, or in combination with another skin filler (examples of which are discussed below) to lessen fine lines around the eye area, forehead, around the mouth, and any other skin surface. Without wishing to be bound to any theory, it is believed that the calcium phosphate particles of this invention have skin filler action that is similar to that described for hyaluronic acid, collagen, and hydroxyapatite. However, by virtue of our the physicochemical characteristics (including size, chemical composition, methods of manufacture, and biocompatibility) of the particles of this invention, as well as its various routes of administration (e.g. topical, subcutaneous, intradermal, intramuscular, intraocular, etc), it is likely to have better functional characteristics (such as no disfigurement of skin after use because particles are generally less than 5 microns in surface diameter and are less likely to agglomerate or clump like the larger particulate fillers), as well as because of non-irritant effects, biocompatibility, non-allergy inducing effects, and longer half-life.

As mentioned, it is also possible to deliver the calcium phosphate particles described above in connection with other skin fillers—with the particles acting as a delivery vehicle, controlled or sustained release mechanism, as an adjuvant, and/or as an additional skin filler. For example, collagen is commonly-used skin filler for treating wrinkles. Renewing the supply of collagen through injections can smooth facial lines, deep smile folds, and scars. It is also successful in enhancing the lip line. Because it is a natural substance, collagen can be injected beneath the skin's surface and it will not be rejected. This treatment typically provides an immediate and visible difference in the appearance of the skin. Injected collagen and fat are primarily used to improve the appearance of the skin's texture and contour, restoring a more youthful looking appearance. They can help fill out deep facial wrinkles, creases and furrows, "sunken" cheeks, skin depressions and some types of scars, and add a fuller look to the lips. The collagen is injected directly into the affected areas.

While bovine collagen has been the undisputed filler of choice for the treatment of facial wrinkles since injectable skin fillers were first introduced, its short-lived results and potential for allergic reactions has limited its potential. Recently, human bioengineered collagen, which is collagen derived from human cells, was approved by the FDA for treating facial wrinkles, acne scarring and lip reshaping. Although human bioengineered collagen is an improvement over bovine collagen because it does not pose an allergy risk, dermatologists continue to seek other improved fillers that can safely and effectively replace hyaluronic acid, one of the primary components lost in aging skin.

Hyaluronic acid is a naturally occurring polysaccharide, which is a normal component of skin. When injected into the skin (typically in a gel form), it binds water and pulls it into the skin, increasing skin plumping and volume and filling in larger folds of skin around the mouth and cheeks. One of the main advantages of hyaluronic acid gel is that it does not pose an allergy risk for patients and there is no risk of transmitting animal diseases by injection.

Some commercial forms of hyaluronic acid are Restylane, Hylaform, and Hylaform Plus. Restylane and Hylaform do not contain a local anesthetic, and patients are more comfortable when topical or local anesthesia is used before treatment. Currently, the trend is to use a combined treatment of hyaluronic acid and collagen to maximize the benefits of each filler. An initial injection of collagen can numb the area, give it support and structure, and stabilize the skin to prevent bruising. When the hyaluronic acid gel is injected afterward, the patient is numb from the collagen injection (reducing the pain) and less likely to bruise, but still receives the benefit of adding volume and water content to the skin. Using these fillers together, two of the major skin components that are lost with skin aging are replaced, can result in a more youthful and natural appearance. Juvederm is another form of hyaluronic acid in injectable form for filling facial lines and wrinkles, enhancing the lips and correcting small facial scars and minor imperfections. Hyaluronic acid is the most popular material used for these purposes and has, over many years, been demonstrated to be both safe and effective.

One of the recent injectable skin fillers on the horizon is polymethylmethacrylate, made from a mixture of micronized plastic spheres and bovine collagen. When polymethylmethacrylate is injected into the skin, the collagen works by holding the synthetic spheres in place until it dissipates after injection—leaving the spheres behind to "prop up" the wrinkles. These spheres stimulate the body's own production of collagen, which then forms around the spheres. The main benefit of polymethylmethacrylate is its permanence, but it also can be its downfall if not injected properly.

For patients who want results that last longer than collagen but not the permanent results of polymethylmethacrylate, a new filler known as hydroxyapatite with a methylcellulose vehicle is being studied as an injectable skin filler. The synthetic compounds used in this filler contain beads of calcium hydroxyapatite, which is a substance used to replace missing bones. If not injected properly, the calcium beads could clump together and result in lumpiness in the treated area.

For example, Radiance (or Radiesse) is one example of a calcium hydroxyapatite filler that is intended to reduce the appearance of facial lines and folds. The product is injectable as is intended to last years, as opposed to months. Radiance consists of calcium hydroxylapatite (a derivative of human bone) microspheres mixed into a gel form. In many studies, this product has been shown to remain soft for long periods of time when injected into soft tissue, such as facial tissue. Radiance (or Radiesse) particles are not FDA approved for cosmetic applications, but are approved for radiographic tissue marking and vocal fold insufficiency. The composition is manufactured from microspheres of calcium hydroxyapatite that are 25 to 45 microns, and up to 150 microns. The particles must be sufficiently large so as to avoid phagocytosis. See U.S. Pat. No. 6,558,612, which also states that that particles smaller than 15 microns become engulfed by the cells and removed from the site by the lymphatic system.

The calcium phosphate particles of this invention may also be used in conjunction with one or more of these skin fillers as a delivery vehicle, as an adjuvant, or as a separate and distinct skin filler. As previously discussed, any of the above components or a similar component may be used as an aesthetic factor in the above example. Those of ordinary skill in the art would be able to determine appropriate concentration and dosage amounts.

II. Other Dermal Stimulators

Calcium phosphate particles may also be delivered in combination with any other injectable skin treatment or dermal stimulator, which may be used as an aesthetic factor in the above example. For example, poly-L lactic acid is not really considered a skin filler, but a "dermal stimulator" because it stimulates the skin cells to make collagen—providing a slow correction over time. It is also possible that the particles of the present invention will also have a prolonged effect. Research studies of poly-L lactic acid for FDA approval of wrinkles are just beginning. One example of a poly-L-lactic acid is Sculptra™ (poly-L-lactic acid), which has been used since 1999 under the trade name New-Fill™. It has been used for restoration and/or correction of the signs of facial fat loss (lipoatrophy) in people with human immunodeficiency virus. Facial fat loss, or lipoatrophy, is the loss of fat beneath the skin, which can result in sunken cheeks, indentations, and hollow eyes. Sculptra™ is injected below the surface of the skin in the area of fat loss. Although not immediate, effects may last up to 2 years after the first treatment session.

Cymetra is a another injectable product, but it is derived from human cells. It is micronized (dry powder) injectable form of AlloDerm tissue used to repair or replace inadequate or damaged tissue caused by surgery, injury, or disease. It also can be used for smoothing deep rhytids, repairing acne scarring, and other facial reconstructive procedures. It is injected beneath the skin and replenishes the very substance that aging depletes. Furthermore, it stimulates ones own tissues/cells to regenerate into the injected "scaffolding." It is as if one is injecting a blueprint beneath the skin directing your own body to repair the skin damaged from aging and the sun. It contains all the elements vital to replace tissue (collagens, elastin, and proteoglycans). Similar to collagen, Cymetra often requires several injections to reach a desired result and will require periodic maintenance injections.

The calcium phosphate particles of this invention may also be used in conjunction with one or more of these dermal stimulators as a delivery vehicle for any aesthetic factors described above, and specifically growth factors, botox, vitamins and minerals, as an adjuvant, or as a separate and distinct stimulator. As previously discussed, any of the above components or a similar component may be used as an aesthetic factor in the above example. Those of ordinary skill in the art would be able to determine appropriate concentration and dosage amounts.

III. Topical Treatments

Another embodiment of the invention includes calcium phosphate particles delivered in combination with a topical treatment, such as a microdermabrasion agent or a chemical peel. Peels and microdermabrasion treatments may greatly improve scars, discolorations, wrinkles, sun-damaged, acne prone and aging skin, and other skin imperfections. Any chemical peel or microdermabrasion agent may be an aesthetic factor in the above example.

Chemical peels use a chemical solution to smooth and improve the texture of the facial skin. Damaged outer layers of skin are removed during the process. A chemical peel is usually performed for cosmetic reasons and may be helpful to those who have wrinkles, blemishes, and uneven skin coloration. Chemical peels may also remove pre-cancerous skin growths, soften acne facial scars, and control acne. TCA (trichloro acetic acid) is a non-toxic chemical that has been used to perform skin peels for many years. The calcium phosphate particles of this invention may serve to reduce the amount of TCA that is required to have the same desired effect as TCA alone; the particles may serve to localize the effects of TCA for a longer time period.

Another skin resurfacing treatment is microdermabrasion, which removes surface dead cells from the skin, and brings forward plump, fresh, healthy cells in conjunction with collagen and elastin tissue. Microdermabrasion is a progressive skin resurfacing treatment that utilizes a hand piece through which powdered micro-crystals are glided across all areas of the face, neck, decollete, back, and/or hands. The crystals are then vacuumed up along with the polished skin. This technique delivers a gentle abrasion to help treat acne scarring, sun damaged skin, lighten brown spots, and treat unevenly textured or oily skin. It can also soften fine lines and wrinkles, decrease the appearance of large pores, and help loosen blackheads.

The crystals may be silica gel crystals, microcrystalline aluminum oxide, alumina crystals, magnesium oxide crystals, sodium bicarbonate crystals, anti-oxidants, or any other commonly used materials for microdermabrasion. They may be of any morphology and grit and may be for either in-home use or for use in a doctor's office only. As previously discussed, any of the above components may be used as an aesthetic factor in the above example, including any other materials that may be used for microdermabrasion. Those of ordinary skill in the art would be able to determine appropriate concentration and dosage amounts.

The calcium phosphate particles of this invention may also be used in conjunction with one or more chemical peels or microdermabrasion agents as a delivery vehicle, as an adjuvant, or as a separate and distinct microdermabrasion agent. As previously discussed, any of the above components or a similar component may be used as an aesthetic factor in the above example. Those of ordinary skill in the art would be able to determine appropriate concentration and dosage amounts.

IV. Delivery of Vitamins and Minerals

Some skin products deliver vitamins, minerals, and alpha-hydroxy-acids to the skin, for example, topical vitamin-C, vitamin-E, and vitamin-A products, moisturizers, broad spectrum sunscreens, and alpha-hydroxy acid products. Any skin vitamin, mineral, herbs or other organic treatment intended to enhance the skin's appearance and texture may be an aesthetic factor in the above example. Treatment may be topical or via injection, into the mesodermal tissues below the skin.

One procedure intended to help deliver topical treatments is the use of "micro-needles" to puncture a layer of the epidermis, which is the main obstruction to penetration of active ingredients. Once this layer has been breached, the active ingredients in the skin care products can reach into the depths of the skin more effectively than by simply applying the products topically. The higher the levels of vitamins that can penetrate into the lower layers of the epidermis, the more collagen can be made, allowing natural collagenesis to occur.

As previously discussed, any of the above components or other similar vitamins or minerals or herbs may be used as an aesthetic factor in the above example. Those of ordinary skill in the art would be able to determine appropriate concentration and dosage amounts.

V. Vein Treatments

Sclerotherapy is a popular vein treatment option for elimination of spider veins and varicose veins. These veins typically appear in legs, but similar treatments may be delivered for rosacea or veins that may appear more pronounced on a patient's face. During the Sclerotherapy procedure, a sclerosing solution is injected into the vein through a micro-needle. Any sclerosing agent known in the art may be used with this invention as an aesthetic factor in the above example. The sclerosing solution causes the vein to blanch (turn white), then gradually to disappear. Sclerotherapy can enhance the appearance of legs, but can also improve the lower extremity circulation. The reduction and elimination of such veins allows the blood flow to be re-routed and also helps diminish aching or fatigue associated with them.

As previously discussed, any of the above components may be used as an aesthetic factor in the above example. Those of ordinary skill in the art would be able to determine appropriate concentration and dosage amounts.

It should also be understood that the activity of the calcium phosphate particles of the present invention, in addition to being an excellent carrier of any of the above-described treatments, may also enhance the activity of the treatments, i.e., by acting as a stimulant or adjuvant. It may also be used to provide a slow release of the composition being delivered. The presence of calcium phosphate in the treated tissues may help increase the activity levels the cells, thereby enhancing the activity of the component to be delivered. Also as discussed above, the calcium phosphate particles of this invention may also act alone, for example, they may be delivered as a skin filler in order to lessen the appearance of wrinkles.

If injected, any pharmaceutically acceptable excipient may be used to carry the particles. If applied topically, the particles may be incorporated into a cream, a gel, an ointment, a lotion, an oil, or any other acceptable delivery vehicle.

What is claimed is:

1. A skin filler for treating one or more skin conditions, consisting essentially of calcium phosphate particles having an average diameter of between about 200 nm to about 4000 nm.

2. The skin filler of claim 1, wherein the average diameter is between about 200 nm to about 2,000 nm.

3. The composition of claim 1, wherein the composition is adapted to be delivered to a layer of skin via topical delivery or via injection.

4. The composition of claim 1, wherein the calcium phosphate particle is smooth without any surface irregularities larger than 100 nm.

5. The composition of claim 1, wherein the calcium phosphate particle is spherical, round, or oval in shape.

6. The composition of claim 1, wherein the calcium phosphate particle is coated or has at least a partial layer of a surface modifying agent covering the particle.

7. The composition of claim 6, wherein the surface modifying agent is a basic sugar, a modified sugar, an oligonucleotide, a carbohydrate, cellobiose, or polyethylene glycol.

8. The composition of claim 1, wherein the calcium phosphate particle is smooth or substantially smooth.

* * * * *